United States Patent
Wessel et al.

[11] Patent Number: 5,948,810
[45] Date of Patent: *Sep. 7, 1999

[54] USE OF R-(+)-α-LIPOIC ACID, R-(–)-DIHYDROLIPOIC ACID AND METABOLITES IN THE FORM OF THE FREE ACID OR AS SALTS OR ESTERS OR AMIDES FOR THE PREPARATION OF DRUGS FOR THE TREATMENT OF DIABETES MELLITUS AS WELL AS OF ITS SEQUELAE

[75] Inventors: Klaus Wessel, Frankfurt; Harald Borbe, Mainz; Heinz Ulrich, Niedernberg; Helmut Hettche, Dietzenbach; Hans Bisswanger, Bodelshausen, all of Germany; Lester Packer, Orinda, Calif.; Amira Klip, Toronto, Canada

[73] Assignee: Asta Medica Aktiengesellschaft, Dresden, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/878,843

[22] Filed: Jun. 19, 1997

Related U.S. Application Data

[62] Division of application No. 08/360,924, Dec. 21, 1994, Pat. No. 5,693,664.

[30] Foreign Application Priority Data

Dec. 21, 1993 [DE] Germany ............... 43 43 593

[51] Int. Cl.$^6$ ............ A61K 31/385; A61K 31/19
[52] U.S. Cl. ............ 514/440; 514/557; 514/866
[58] Field of Search ............ 514/440, 557, 514/866

[56] References Cited

U.S. PATENT DOCUMENTS 4,678,670 7/1987 Tomic ................... 424/718

FOREIGN PATENT DOCUMENTS 42 18 572 A1 12/1993 Germany.

OTHER PUBLICATIONS

Natraj et al. Chemical Abstracts (101) 495u, 1984.
Gandhi et al. Chemical Abstracts (104) 161793s, 1986.
Biochem. Biophys. Res. Commun., Bd. 203, Nr. 1, 1994, pp. 99–104, T. Kawabata et al., Alpha–lipoate can protect against glycation of serum albumin, but not low density lipoprotein.
Naunyn–Schmiedebergs Arch. Pharmacol. Bd. 349, Nr. supl., 1994, Seite r8, C. Bonaventura et al. "In Vitro Action of the enantiomers of alpha–lipoic acid".
Nervenarzt, Bd. 59, Nr. 1, 1988, pp. 36–44, J. Jorg et al., "Zur Medikamentosen Behandlung der diabetischen polyneuropathie mit der alpha–liponsaure oder vitamin–b–praparaten".
Dtsch. Zschr. Verdau. Stoffwechselkr., Bd. 44, Nr. 4, 1984, pp. 173–180, J. Studt et al., "die diabetische autonome neuropathie des herzens und ihre behandlung mit thioctsaure".
The Merck Index, Windholz, et al., pp. 723, 724, ab No. 4866 (1983).
S.S. Wagh et al.; Mode of Action of Lipoic Acid in Diabetes; Journal of Biosciences; Mar. 1987; pp. 59–74; vol. 11, No. 1–4.
Yuichiro J. Suzuki et al.; Lipoate Prevents Glucose–Induced Protein Modifications; Free Radiacl Res. Commun.; 1992; pp. 211–217, vol. 17; No. 3.

*Primary Examiner*—Kevin E. Weddington
*Attorney, Agent, or Firm*—Pillsbury Madison & Sutro LLP

[57] ABSTRACT

The invention relates to the use of R-(+)-α-lipoic acid, R-(–)-dihydrolipoic acid or their metabolites, salts, esters and amides for the synthesis of drugs for the treatment of diabetes mellitus of types I and II, compensated and decompensated insulin resistance and sequelae or late complications of diabetes mellitus, such as cataracts, polyneuropathy, nephropathy, as well as sequelae or late complications of insulin resistance.

1 Claim, No Drawings

USE OF R-(+)-α-LIPOIC ACID, R-(-)-DIHYDROLIPOIC ACID AND METABOLITES IN THE FORM OF THE FREE ACID OR AS SALTS OR ESTERS OR AMIDES FOR THE PREPARATION OF DRUGS FOR THE TREATMENT OF DIABETES MELLITUS AS WELL AS OF ITS SEQUELAE

This is a division of application Ser. No. 08/360,924, filed Dec. 21, 1994, now U.S. Pat. No. 5,693,664.

FIELD OF INVENTION

The invention relates to drugs for the treatment of diabetes mellitus types I and II and its late complications and sequelae or of subclinically existing insulin resistance and its late complications and sequelae, as well as to their synthesis.

R-(+)-α-lipoic acid is the physiologically occurring enantiomer of 1,2-dithiocyclopentane-3-valeric acid. R-(+)-α-lipoic acid is a coenzyme of α-ketoacid dehydrogenases (pyruvate dehydrogenase, α-ketoglutarate dehydrogenase, etc.) and acts at a key site in the sugar and energy metabolism of the cell. In its function as an intramolecular redox system, it is oxidized (α-lipoic acid) and reduced (dihydrolipoic acid).

The racemate is used as a 50/50 mixture of R-(+)-α-lipoic acid and S-(-)-α-lipoic acid for the treatment of diabetic and alcoholic polyneuropathy, as well as for the treatment of Amanita phalloides poisoning and of chronic and alcoholic liver diseases.

It is well known that the pharmacological properties of the enantiomers of α-lipoic acid differ, for example, with respect to their anti-inflammatory and analgesic effect (European patent EP-A 427 247). It is furthermore reported in the literature that R,S-(+,-)-α-lipoic acid has a blood sugar-lowering effect in the case of alloxan-induced diabetes in the animal model. In this connection, it has not been resolved whether this effect due to interference with the secretion of insulin or directly due to the activation of the pyruvate dehydrogenase (C. V. Natraj et al., J. Biosci. vol. 6(1), 37–46 (1984)). Metabolic deviations resulting from diabetes, such as hyperglycemia, ketonemia, ketonuria, reduced glycogen in the tissue and a decreased synthesis of fatty acids in the liver are corrected in animal experiments by the administration of lipoic acid (S. S. Wagh, C. V. Natraj et al., J. Biosci. vol. 11, 59–74 (1987)).

It is furthermore known that oxidative stress is associated with a promoting role in late complications of diabetes and that an adjuvant antioxidant therapy (with thioct acid) can lead to a regression of the late complications of diabetes (W. Kaehler et al., Innere Medizin 48, (1983) 223–232).

In vitro experiments with thioct acid (material from the Calbiochem Co. (racemate)) have confirmed that it increases the glucose assimilation by muscles. Time studies show that, contrary to the stimulating effect of insulin on glucose assimilation, the effect of thioct acid on rat diaphragms can be recognized in vitro only after a prolonged incubation. According to Haugaard, the mechanism of action of thioct acid appears to be unlike that of insulin. Its effect is additive to that of insulin (N. and E. S. Haugaard, Biochim. Biophys. Acta 222 (1970) 582–586). However, in this reference there is also no statement concerning the different effects of R- and S-thioct acids. Diabetes mellitus is a disease with an insulin deficiency or a resistance to the action of insulin (decompensated insulin resistance). Subsequently, numerous metabolic disorders particularly of the carbohydrate and fat metabolism occur even in the case of still compensated insulin resistance (reduced effect of insulin without clinically manifest diabetes type II). In the long run, these disorders can lead to coma and death. The insulin resistance, as well as the elevated blood sugar and the impaired fat metabolism participate in the development of sequelae and late complications (such as cataracts, neuropathies, nephropathies). The elevated blood sugar can be treated by substitution with insulin and, in mild cases, by oral antidiabetic drugs. Up to the present, there has not been a recognized, therapeutic possibility for intervening in the insulin resistance itself.

A basic disorder in the case of diabetes and insulin resistance lies in the glucose assimilation by muscle cells. In this connection, particularly within the framework of insulin resistance, it is important to treat the glucose assimilation not by the administration of insulin or by pharmaceutical drugs stimulating the excretion of insulin, but by mechanisms independent thereof (H. U. Haering, H. Mehnert, Diabetologica 36, 176–182, 1993).

The metabolization, within the framework of mitochondrial energy metabolism, necessary after the cellular assimilation of glucose, is a further, necessary step, particularly in the case of a defective glucose utilization within the framework of insulin resistance. A key enzyme is the pyruvate dehydrogenase.

Diabetics show increased glycosilation and oxidation of proteins with corresponding negative consequences for the patients (Z. Makita et al., Science 258, 651–653, 1992).

The finding that specifically R-(+)-α-lipoic acid is suitable for the treatment of diabetes mellitus and insulin resistance, while the S-(-)-α-lipoic acid practically is not usable for this, is new and unexpected and not inferable by those skilled in the art. Our own investigations have shown that, in animal experiments, the key enzyme, pyruvate dehydrogenase, surprisingly was inhibited by the S-(-)-α-lipoic acid.

It is therefore an object of the invention to make available drugs for the treatment of compensated and decompensated insulin resistance and, with that, of associated diseases and sequelae, or of diabetes mellitus and its sequalae and late complications. The assimilation of blood sugar in the tissue is promoted. This is of clinical relevance in the case of pathological disorders of the control of blood sugar adjustment, as in the case of diabetes mellitus types I and II, or in the case of disorders in insulin sensitivity of the tissue (insulin resistance). This applies in the case of monotherapy, as well as in the case of a combination with other drugs for the treatment of diabetes mellitus or of insulin resistance, such as oral antidiabetic drugs and, in particular, insulin. The objective of the treatment can also be a savings in the therapeutically administered insulin or in other antidiabetic drugs, as well as a lowering in the pathologically elevated endogenous insulin level. Furthermore, late complications or sequelae of diabetes mellitus or of insulin resistance can also be affected therapeutically by the treatment of the basic diseases.

Surprisingly, it has now been found that preferably R-(+)-α-lipoic acid proves to be suitable for the treatment of diabetes mellitus types I and II and its sequelae and late complications and for the treatment of subclinically and clinically manifest insulin resistance and its sequelae.

PHARMACOLOGICAL EXAMPLES

1. Pyruvate Dehydrogenase Activity After Chronic Administration in Different Tissues of the Spontaneously Diabetic Rat Results Trend After Two Administrations Lowered by S-(−)-α-lipoic acid, increased by R-(+)-α-lipoic acid.

Description of the Experiment

After the manifestation of the diabetes, spontaneously diabetic rats (BB-Wol BB, of the Moellegard Company, Denmark, n=10/group) received 0.3 mL of neutral 0.12 M (corresponding to 50 mg/kg of body weight) R-(+)-α-lipoic acid or S-(−)-α-lipoic acid daily, administered in the vein of the tail. A control group received physiological salt solution. After 7 days, the animals were sacrificed. The pyruvate dehydrogenase activity was determined in the heart muscle. The tissue was homogenized.

Measurement of the Pyruvate Dehydrogenase Activity

Test Principle

The extinction of the reduced coenzyme is measured at 339 nm in cuvettes with a Shimadzu UV 210 Detector at 37° C. The isolation of the enzyme complex (R. Koeplin, Ph.D. Thesis, University of Tuebingen, FRG, 1988, C. J. Stanley, R. N. Perham, Biochem. J. 191, 147–154, 1980) and the enzyme assay (O. H. Lowry et al. J. Biol. Chem. 256, 815–822, 1951) were carried out as described. The protein was measured by the method of Lowry (N. Bashan et al., Am. J. Physiol. m262 (Cell Physiol. 31): C682–690, 1992).

2. Glucose Assimilation in Muscle Cells Under Insulin (Klip)

Results

Glucose Assimilation

Compared to the S enantiomer, the R enantiomer (2.5 mM) stimulates glucose assimilation by a factor greater than 2; at the same concentration the S enantiomer is less effective.

| | Glucose Assimilation in Muscle Cells | | |
|---|---|---|---|
| Incubation Time | Glucose Assimilation Control (pmol/mg × min) | Glucose Assimilation R (pmol/mg × min) | Glucose Assimilation S (pmol/mg × min) |
| 15 | 15.1 ± 0.4 | 16.7 ± 0.6 | 16.3 ± 0.3 |
| 30 | 12.1 ± 0 | 15.9 ± 0.9 | 14.8 ± 0.7 |
| 60 | 16.5 ± 0.4 | 26.1 ± 0.9 | 21.6 ± 0.4 |
| 120 | 15.7 ± 0.6 | 27.0 ± 0.4 | 20.5 ± 0.8 |

| | Glucose Assimilation in Muscle Cells in Conjunction with Insulin (200 nM) R-(+)-α-Liponic Acid (2.5 mM) | | | |
|---|---|---|---|---|
| Incubation Time (min) | Glucose Assimilation Control (pmol/mg × min) | Glucose Assimilation R-(+)-α-Lipoic Acid (pmol/mg × min) | Glucose Assimilation Insulin (pmol/mg × min) | Glucose Assimilation Insulin + R-(+)-α-Lipoic Acid (pmol/mg × min) |
| 15 | 20.0 ± 0.9 | 23.2 ± 0.5 | 24.7 ± 0.9 | 25.1 ± 0.6 |
| 30 | 18.1 ± 0.6 | 21.1 ± 0.4 | 21.6 ± 0.4 | 21.1 ± 0.2 |
| 60 | 18.0 ± 0.6 | 25.7 ± 0.5 | 23.7 ± 0.5 | 26.2 ± 0.7 |

The effect of the R enantiomer is comparable to that of insulin (200 nM); however, the two effects are not additive.

In contrast to R-(+)-α-lipoic acid, the S enantiomer decreases the effect of insulin.

| | Glucose Assimilation in Muscle Cells in Conjunction with Insulin (200 nM) S-(−)-α-Lipoic Acid, (2.5 mM) | | | |
|---|---|---|---|---|
| Incubation Time (min) | Glucose Assimilation Control (pmol/mg × min) | Glucose Assimilation S-(−)-α-Lipoic Acid (pmol/mg × min) | Glucose Assimilation Insulin (pmol/mg × min) | Glucose Assimilation Insulin + S-(−)-α-Lipoic Acid (pmol/mg × min) |
| 15 | 14.5 ± 0.3 | 14.8 ± 0.4 | 17.7 ± 0.3 | 16.0 ± 0.4 |
| 30 | 13.8 ± 0.5 | 13.3 ± 0.4 | 16.3 ± 0.5 | 15.7 ± 0.3 |
| 60 | 15.6 ± 0.5 | 16.0 ± 0.2 | 22.3 ± 0.5 | 19.8 ± 1.1 |

Description of the Experiment

The tissue muscle cells (L6 myotubes) were prepared in 24-hole plates and differentiated. After incubation with the test substances, an assay was carried out to determine hexose assimilation ($^3$H-2-desoxyglucose, 10 μM, 10 minutes). Insulin was added at a concentration of 200 nM and the α-lipoic acid enantiomers were added at a concentration of 2.5 mM. After the cells were washed and then lysed with NaOH, the radioactivity absorbed was measured in a counter. Parallel experimental batches were carried out with cytochalasin-B, in order to determine the glucose transporter-dependent glucose translocations. The results can be expressed as pmol/min×mg of protein. The experiments were carried out by the method described by U. M. Koivisto et al., J. Biol. Chem. 266, 2615–2621, 1991.

4. Effect on the Translocation of Glucose Transporters

Results

R-(+)-α-Lipoic acid stimulates the translocation of glucose transporters (Glut 1 and GLUT 4) from the cytosol to the plasma membrane; this is equivalent to an activation. S-(−)-α-Lipoic acid has no effect or has an inhibiting effect and appears to lower the total content of glucose transporters in the cell (GLUT4). A translocation of the glucose transporters corresponds to an activation of the most important cellular glucose assimilation mechanisms. Insulin also stimulates the glucose transporter translocation.

| Treatment | Plasma Membrane (relative units) | Light Microsomal Fraction (relative units) |
|---|---|---|
| Effect of Enantiomers of α-Lipoic Acid (2.5 mM) on the Translocation of GLUT1 Glucose Transporters in L6-Myotubes | | |
| Control | 1.00 | 1.00 |
| R-(+)-Lipoate | 1.56 ± 0.25 | 0.46 ± 0.06 |
| S-(−)-Lipoate | 0.93 ± 0.37 | 0.38 ± 0.09 |
| Insulin | 1.07 ± 0.14 | 0.68 ± 0.10 |
| Effect of Enantiomers of α-Lipoic Acid (2.5 mM) on the Translocation of GLUT4 Glucose Transporters in L6-Myotubes | | |
| Control | 1.00 | 1.00 |
| R-(+)-Lipoate | 1.40 ± 0.08 | 0.59 ± 0.04 |
| S-(−)-Lipoate | 0.84 ± 0.37 | 0.71 ± 0.11 |
| Insulin | 1.38 ± 0.09 | 0.75 ± 0.11 |

Description of the Experiment

L6 myotubes in 15 cm dishes (n=4 to 5) were enlisted and incubated for one hour with 2.5 mM lipoate in MEM with 5 mM of glucose and 2% of fetal bovine serum. The cells were removed, homogenized and worked up in fractions (4°

C.). The working up was carried out in an HEPES buffer with a defined addition of protease inhibitor. The cell fractions were obtained in 6 defined centrifuging steps. The fractions were added to a 10% polyacrylamide gel for a Western Blot analysis. The glucose transporters were determined with anti-GLUT1 and anti-GLUT4 antibodies using iodine-labeled protein A and autoradiographic detection.

5. Effect on the Cellular Content of Glucose Transporters

Results

After four hours of incubation, R-(+)-α-lipoic acid increases the cellular content of GLUT1 and GLUT4 glucose transporters. S-(−)-α-Lipoic acid has no effect or lowers the cellular content.

Effect of Liponic Acid Enantiomers (2.5 mM) after 4 Hours of Incubation on the Content of Glucose Transporters in L6-Myotubes

| Treatment | GLUT1 (arbitrary units) | GLUT4 (arbitrary units) |
| --- | --- | --- |
| Control | 1.00 | 1.00 |
| R-(+)-Lipoate | 1.81 ± 0.01 | 1.55 ± 0.24 |
| S-(−)-Lipoate | 1.08 ± 0.01 | 0.79 ± 0.47 |

Description of the Experiment

L6 myotubes were incubated for 4 hours with 2.5 mM lipoic acid enantiomers in an MEM medium with 2% fetal bovine serum and 5 mM glucose. The glucose transporters were detected as described above. The membrane fraction is obtained after a single centrifugation at 210,000 g.

6. Diabetes Induced Tissue Damage

Results

In a diabetes animal model (streptozotocin-induced diabetes), it was now surprisingly observed that R-thioct acid corrects numerous pathologically changed parameters (glycosilated hemoglobin, protein oxidation), whereas the S enantiomer exhibits a lesser effect to no effect. Surprisingly and additionally, the mortality of the animal groups in the group exposed to the S enantiomer was increased, while the mortality in the group with the R enantiomer was reduced in comparison to the control.

Glycosilated Hemoglobin

| Experimental Group | % Glycosilated Hemoglobin |
| --- | --- |
| Control | 9.7 ± 1.5 (n = 8) |
| R-Thioct acid diet | 8.4 ± 1.3 (n = 11) |
| S-Thioct acid diet | 10.7 ± 2.1 (n = 6) |

Protein-Carbonyl Formation in the Lens and Liver

| Experimental Group | nmol Carbonyl/mg Protein Lens | Carbonyl/mg Protein Liver (% of Control) |
| --- | --- | --- |
| Control | 0.513 ± 0.051 (n = 3) | 100. ± 8.9 (n = 6) |
| R-Thioct acid diet | 0.429 ± 0.063 (n = 3) | 73.2 ± 17.8 (n = 6) |
| S-Thioct acid diet | 0.554 ± 0.022 (n = 3) | 90.3 ± 10.7 (n = 6) |

Mortality in Streptozotocin-treated Rats

| Experimental Group | % Mortality |
| --- | --- |
| Control | 33.3 |
| R-Thioct acid diet | 8.3 |
| S-Thioct acid diet | 50.0 |

Description of the Experiment

Thioct acid enantiomers were administered for 14 weeks by mouth, together with the food (1.65 g/kg of food), to female Wistar rats (n=3 to 6/group) in separate groups.

In the eighth week, streptozotocin diabetes was induced in the animals. Six weeks after the induction of the diabetes, the surviving animals were sacrificed. Tissue was taken and analyzed.

R-(+)-α-Lipoic acid can thus be regarded a highly specific effective drug for the treatment of diabetes mellitus types I and II as well as of disorders in the insulin sensitivity of the tissue (insulin resistance) and of sequelae and late complications. Moreover, R-(+)-α-lipoic acid can be used in the case of diseases with a reduced glucose transporter content or a defective glucose transporter translocation, such as congenital or hereditary glucose transporter deficiency. Likewise, R-(+)dihydrolipoic acid, the metabolites such as bisnor- and tetranor-lipoic acid and their salts, esters and amides can be used.

The following, for example, come into consideration as indications for the use of drugs, which contain the materials mentioned:

diabetes mellitus types I and II subclinically and clinically manifest insulin resistance and their sequelae (compensated and decompensated insulin resistance)

cataracts polyneuropathies nephropathies glucose transporter deficiency

The R-(+)-α-lipoic acid, R-(−)dihydrolipoic acid or their metabolites (such as bisnor- or tetranor-lipoic acid), as well as their salts, esters, amides are synthesized by known methods (see, for example, German Offenlegungsschrift 41 37 773).

The invention also relates to the use of drugs, which contain the optically pure R-(+)-α-lipoic acid, R-(−)-dihydrolipoic acid or their metabolites as well as their salts, esters and amides, for the treatment for the diseases named above.

PHARMACEUTICAL EXAMPLES

The amounts by weight, given in the patent, relate in each case to the pure optical isomer and not to the salts. When salts, esters or amides are used, the weights must be adapted correspondingly to the changed molecular weights.

The salts are synthesized by known methods (see also Patent EP-A 901213405). The pharmaceutical preparations generally contain 3 to 5 mg of the compounds used pursuant to the invention as a single dose. After repeated administrations, the effective level attained in the body should be between 0.1 and 100 mg/kg of body weight.

The material is administered in the form of tablets, chewable tablets, sucking tablets, pills, capsules, granulates, coated tablets, effervescent tablets, effervescent powders, finished drink solutions, liquid forms for parenteral administration and aerosols. Finished drink solutions and liquid forms for parenteral administration can be alcoholic or aqueous solutions, suspensions and emulsions.

Preferred embodiments are, for example, tablets, which contain between 10 mg and 2 g of active substance, as well as solutions, which contain the active substance in amounts of between 1 mg and 200 mg per mL of liquid.

The following may be named as single doses of the active ingredient:

a. oral forms: 10 mg to 3 g
b. parenteral forms (intravenous or intramuscular): 10 mg to 12 g
c. inhalants: 10 mg to 2 g.

The doses a) to c) can be administered, for example, 1 to 6 times daily or as an intravenous drip.

EMBODIMENTS

Example 1

Tablets With 100 mg of R-(+)-α-Lipoic Acid

R-(+)-α-Lipoic acid (250 g) is triturated uniformly with 750 g of microcrystalline cellulose. After the mixture is screened, 250 g of starch (Starch 1500/Colorcon), 732.5 g of lactose, 15 g of magnesium stearate and 2.5 g of highly dispersed silica are admixed and the mixture is pressed into tablets weighing 800.0 mg. One tablet contains 100 mg of R-(+)-α-lipoic acid. If necessary, the tablets can be coated in a conventional manner with a film, which is soluble or permeable to gastric juices.

Example 2

Ampules With 250 mg of R-(+)-α-Lipoic Acid as Trometamol Salt in 10 mL of Injection Solution R-(+)-α-Lipoic acid (250 g), together with 352.3 g of trometamol (2-amino-2-(hydroxymethyl)-1,3-propylene glycol) is dissolved with stirring in a mixture of 9 liters of water for injection purposes and 200 g of 1,2-propylene glycol. The solution is made up to 10 liters with water for injection purposes and subsequently filtered through a glass fiber prefilter and then through a membrane filter with a pore size of 0.2 μm. The filtrate (10 mL amounts) is filled under aseptic conditions into 10 mL ampules. In 10 mL of injection solution, 1 ampule contains 250 mg of R-(+)-α-lipoic acid as the trometamol salt.

Example 3

Ampules With 250 mg of R-(−)-Dihydrolipoic Acid in 10 mL of Injection Solution

Trometamol (60 mg) and 1 g of the disodium salt of ethylenediaminetetraacetic acid are dissolved in 1.8 liters of water for injection purposes. Nitrogen is bubbled for 30 minutes through the solution. While the bubbling of nitrogen is continued, 2 g of sodium disulfite and subsequently 50 g of R-(−)-dihydrolipoic acid are dissolved in the mixture. The solution is made up to a volume of 2 liters with water for injection purposes, through which nitrogen has been bubbled. After careful mixing, the solution is filtered through a membrane filter with a pore size of 0.2 μm and the filtrate is filled into 10 mL ampules under aseptic conditions, nitrogen being bubbled through the filtrate before and after it is filled into the ampules. One ampule contains 250 mg of R-(−)-dihydrolipoic acid as the trometamol salt in 10 mL of solution.

We claim:

1. A process for the treatment of diabetes mellitus type I or type II comprising administering to a patient an effective amount of pure R-(+)-α-lipoic acid, pure R-(−)-dihydrolipoic acid, amides, salts, metabolites or esters thereof.

* * * * *